United States Patent [19]
Lerch

[11] Patent Number: 6,057,301
[45] Date of Patent: May 2, 2000

[54] HYPERHYDRATED CITICOLINE, PROCESS AND USE

[75] Inventor: Gregory H. Lerch, Westford, Mass.

[73] Assignee: Interneuron Pharmaceuticals, Inc., Lexington, Mass.

[21] Appl. No.: 09/219,595

[22] Filed: Dec. 23, 1998

Related U.S. Application Data

[60] Provisional application No. 60/068,733, Dec. 24, 1997.

[51] Int. Cl.[7] .................................................. A01N 43/04
[52] U.S. Cl. ................ 514/49; 514/50; 514/51; 514/951; 424/489
[58] Field of Search ................ 424/78, 489; 536/26.23; 514/49, 50, 51, 951

[56] References Cited

U.S. PATENT DOCUMENTS

| | | | |
|---|---|---|---|
| 3,687,932 | 8/1972 | Nakamachi et al. | 260/211.5 R |
| 4,772,463 | 9/1988 | Zappia et al. | 424/78 |
| 4,789,666 | 12/1988 | Gennari | 514/51 |
| 4,861,591 | 8/1989 | Weierstall et al. | 424/690 |
| 5,688,510 | 11/1997 | Nakamichi et al. | 424/195.1 |
| 5,801,160 | 9/1998 | Sandage et al. | 514/49 |
| 5,811,547 | 9/1998 | Nakamichi et al. | 540/589 |

OTHER PUBLICATIONS

Secades, J.J. and Frontera, G.; CDP–Choline: Pharmacological and Clinical Review. Meth Find Exp Clin Pharmacol 1995; 17 (Suppl B) pp. 1–54.

*Primary Examiner*—James O. Wilson
*Attorney, Agent, or Firm*—Gilberto M. Villacorta; Pepper Hamilton LLP

[57] ABSTRACT

A hyperhydrated form of citicoline and its formulations, which exhibits desirable characteristics, including crystal formation, moisture resistance, improved storage stability, and formulation versatility, is disclosed. Methods of preparing the citicoline hyperhydrate and its use in the manufacture of stable pharmaceutical dosage forms are also described.

28 Claims, 7 Drawing Sheets

HYPERHYDRATED CITICOLINE, PROCESS AND USE

RELATED APPLICATION

The present application claims the benefit of the priority date of co-pending Provisional Application Ser. No. 60/068,733, filed Dec. 24, 1997, the complete disclosure of which is incorporated by reference herein.

1. FIELD OF THE INVENTION

The present invention relates to a novel formulation of citicoline, a compound that is also known as CDP-choline or cytidine diphosphate choline. In particular, a new, stable, hyperhydrated, crystalline form of citicoline is disclosed. Methods of preparing this citicoline hyperhydrate are described, including stable pharmaceutical forms and/or formulations thereof.

2. BACKGROUND OF THE INVENTION

Citicoline is a compound represented by formula (I).

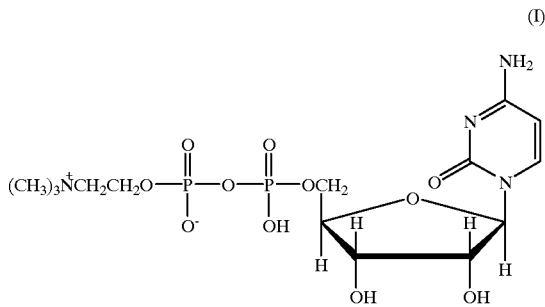

Citicoline is amorphous, hygroscopic powder, which has therapeutic utility, for example, as a cerebroprotectant, or a neuroprotectant. In particular, citicoline is beneficial the victims of ischemic stroke, head trauma, and, possibly, neurodegenerative disease. In addition, citicoline is used to treat unconsciousness resulting from cranial trauma, hemorrhages, cerebral thrombosis, and cerebropathies due to atherosclerosis (Secades J J. CDP-choline: pharmacological and clinical review. Methods Find Exp Clin Pharmacol 1995 Oct; 17 Suppl B:2–54).

For pharmaceutical applications, citicoline has been formulated in solution, suitable for parenteral administration, usually intravenous administration. However, currently available solid forms of citicoline suffer from a number of drawbacks. Commercially available forms of citicoline (or its salt, typically citicoline sodium) range in water content to not more than 5% by weight (relative to the citicoline), as determined by water loss on drying or by Karl Fischer moisture analysis. Normally, the amount of water present in commercially available forms of citicoline sodium ranges between 2% to 4% by weight. Such conventional solid forms of citicoline are unstable on exposure to atmospheric humidity. This instability, due to the hygroscopic nature of the molecule, is carried over to solid dosage formulations, such as tablets, capsules and the like, which contain conventional citicoline.

Because of its susceptibility to moisture and stated product specifications relating to water content, citicoline must be processed under special conditions, including a low humidity environment, to provide and maintain a relatively low water content. Manufacturers of pharmaceutical drug products must be able to show that their final dosage forms are stable and remain within certain stated specifications, including water content, hardness and physical integrity. To protect the compound against moisture during normal storage conditions special packaging materials must be used, including aluminum foil pouches or double-walled polyethylene bags equipped with desiccants. For example, U.S. Pat. No. 4,861,591 discloses a hard gelatin capsule consisting essentially of several moisture impervious outer layers of humidity-resistant excipients encapsulating the hygroscopic active ingredient.

Indeed, during formulation, citicoline sodium must be coated with excipients, such as castor oil and talc, to help retard the sorption of moisture. Despite that the tablets ultimately sorb water, swell and crack, limiting the shelf life of the product. Hence, much, if not all, effort in the art has been directed to insulating citicoline, its salts and its pharmaceutical dosage forms against unwanted exposure to atmospheric humidity. Various other methods are employed in the prior art to obtain stable forms of hygroscopic or deliquescent pharmaceuticals like citicoline.

U.S. Pat. No. 5,688,510 issued to Nakamichi et al., discloses processing en block by means of multi-screw extruder wherein a physiologically inert powdery additive and a macromolecular additive are added to the unstable active ingredient. While this process is claimed to be applicable to citicoline it is unrelated to the instant invention since it is based on totally different physical and chemical principles.

U.S. Pat. No. 5,811,547 issued to the same group of inventors, Nakamichi et al., discloses yet another method of obtaining stable pharmaceuticals by means of inducing a transition in crystalline state whereby a drug of interest passes through two separate zones maintained at different temperatures. Again, the disclosed process has nothing in common with the instant invention, either by principle or by design.

U.S. Pat. No. 3,687,932, issued to Nakamachi et al., discloses crystalline CDP-choline monohydrate that is allegedly stable when the water content in the formulation is around 5–6%. This disclosure, however, fails to demonstrate or suggest that stable crystalline forms of citicoline with higher hydration levels might exist. Indeed, all currently manufactured forms of citicoline contain no more than 5% of water by weight. Thus, the prevailing consensus dominating the prior art is that higher levels of water would render citicoline unstable and unusable for manufacturing pharmaceutical formulations.

Accordingly, it would be a significant advancement in the art to provide a novel form of citicoline, along with its solid tablet, capsule and like solid forms, having improved stability, structural integrity and other physicochemical, manufacturing, or pharmacological benefits over currently available forms. More particularly, it would advance the art to provide a solid form of citicoline that does not suffer detrimental consequences from exposure to atmospheric moisture and whose solid dosage forms exhibit improved physical storage stability. Similarly, it would be a welcome contribution and advancement to provide processes or methods for preparing such stable crystalline forms of citicoline, along with storage stable capsules, tablets, gelcaps and the like containing citicoline.

Such a "stabilized" form of citicoline is discovered by the present inventor. In particular, a hyperhydrated form of citicoline is provided by the instant invention, which substantially eliminates the shortcomings of conventional citicoline and its conventional formulations. Hence, the poor or problematic storage characteristics of pharmaceutical dosage forms of conventional citicoline, at least, are substantially eliminated by the present invention. While not wishing to be bound by theory, it is understood that the newly discovered hyperhydrated form of citicoline is essentially citicoline tetrahydrate. A pharmaceutical composition may, however, contain small amounts of lesser or higher hydrated forms of citicoline, e.g., monohydrate, dihydrate, trihydrate, etc. However, due to the high moisture content these forms are unlikely to be encountered. It is also understood that citicoline tetrahydrate is a hyperhydrated form of citicoline, and these two terms are used hereinafter interchangeably. The advantages that are offered by this new form of citicoline, as well as processes for making this hyperhydrated citicoline, are described in greater detail, below. It is important to note that the "stabilized" formulations of the present invention can be prepared by using the hyperhydrated form of citicoline, as an initial ingredient or starting material, or by incorporating an adequate amount of total water into the dosage form to ensure the in situ formation of the citicoline hyperhydrate from the conventionally obtained citicoline, as starting material for the desired formulation.

3. SUMMARY OF THE INVENTION

The present invention relates to the discovery that citicoline, in the presence of the proper amount of water, forms a putative hyperhydrated state, which gives rise to very stable, crystalline formulations of the citicoline drug. In particular, the present invention is directed to a solid hyperhydrated form of citicoline having water content of not less than about 10% by weight (w/w). In preferred embodiments, the citicoline hyperhydrate has a water content of not less than about 10.5% by weight (w/w), more preferably, not less than about 11% by weight (w/w) and most preferably, not less than about 12% by weight (w/w). Still other embodiments of the invention contain formulations of citicoline in which the water content of the formulation ranges from about 10% to about 15% by weight (w/w), based on the amount of citicoline present. In preferred formulations, the water content ranges from about 10.5% to about 14% by weight (w/w), more preferably, a water content that ranges from about 11% to about 13% by weight (w/w), most preferably, a water content that ranges from about 12% to about 13% by weight (w/w). Crystalline citicoline having a water content of not less than about 10% by weight (w/w) is preferred and provided by the methods described herein.

The present discovery applies to any citicoline free acid, salt, or ester. A salt of citicoline may contain an ion consisting of sodium, potassium, calcium, iron, ammonium, di-lower-alkyl ammonium, tri-lower-alkyl ammonium. Preferred forms of citicoline include, but are not limited to, its alkaline or alkaline-earth salt, preferably the lithium, sodium, potassium, magnesium, or the like salt. Where the sodium salt of citicoline is used in the formulation of the invention, a water content ranging from about 12% to about 13% by weight (w/w) is advantageous, preferably, a water content of about 12.5% by weight (w/w).

Other preferred salts of citicoline can be used as well. For example, one can use CDP-choline salts formed upon addition of sulfonic acid as disclosed in detail in U.S. Pat. No. 4,789,666. Other acid addition salts can be imagined in which the salt-forming moiety is hydrochloric acid, hydrobromic acid, sulfuric acid, acetic acid, triflouroacetic acid, citric acid, lactic acid, malonic acid, tartaric acid, acrylic acid, methacrylic acid, malic acid, maleic acid, fumaric acid, benzoic acid, salicylic acid, cinnamic acid, methanesulfonic acid, benzenesulfonic acid, toluenesulfonic acid, nicotinic acid, or suitable combination thereof.

Other "ester" forms of CDP-choline can be used as preferred embodiment of this invention. For example, U.S. Pat. No. 4,772,463 discloses CDP-choline which is covalently bonded to a polymeric matrix containing carboxy groups, by means of biodegradable amide bonds involving carboxy groups and the NH2 group in position 4 on the aromatic nucleus of the CDP-choline, and/or by means of biodegradable ester bonds between carboxy groups and the OH groups in 2' and 3' of ribose. The polymeric matrix can be selected from the group consisting of polyacrylic acids, polymethacrylic, polymaleic, polyaminoacids, or copolymers of polymerizable acids with acrylic acids or acrylamide.

A further object of the present invention is to provide a hyperhydrated form of citicoline which exhibits substantially at least the peaks marked with the "A" arrows shown in the X-ray powder diffraction pattern of FIG. 4. A preferred citicoline hyperhydrate exhibits substantially at least the peaks marked with the "A" arrows and the "B" arrows as shown in the X-ray powder diffraction pattern of FIG. 4. The hyperhydrated citicoline of the invention preferably comprises a citicoline sodium hyperhydrate or citicoline potassium hyperhydrate. Alternatively, these hyperhydrates are formed in situ by providing an adequate amount of water in the desired formulation to allow for the formation of the hyperhydrate.

Yet another object of the present invention is to provide a citicoline that exhibits a change in weight of less than about 2% upon exposure to moisture conditions having a relative humidity (RH) ranging from about 10% to about 80%.

Consistent with the objectives of the present invention, a formulation is provided which comprises citicoline having a total water content sufficient to provide an amount of water which is not less than about 10.5% by weight relative to the amount of citicoline present in the formulation. Pharmaceutically acceptable carriers can be utilized in the present invention. Other embodiments include formulations having a total water content sufficient to provide an amount of water which is not less than about 11.5% by weight relative to the amount of citicoline present in the formulation, more preferably, a total water content sufficient to provide an amount of water which is not less than about 12.5% by weight relative to the amount of citicoline present in the formulation. While many solid formulations can be contemplated, including but not limited to capsules, cachets, tablets, pills, or lozenges, the oral formulations are commercially more attractive.

According to the present invention, the foregoing and other objects are achieved in part by a process for producing a citicoline tablet comprising about 10% to about 15% (w/w) water comprising mixing a citicoline hyperhydrate with pharmaceutically acceptable excipients or mixing a conventional citicoline hypohydrate with pharmaceutically acceptable excipients along with an amount of water adequate to permit the formation of the hyperhydrate in situ. In addition to conventional excipients the formulation may or may not contain other additive agents or groups consisting of a binder, a disintegrator, a lubricant, a glidant, a preservative, an antioxidant, an isotonizing agent, a buffer, a coating agent, a granulating agent, a filler, a bulking agent, a plasticizer, a corrigent, a solution adjuvant, a diluent, a thickener, a base, a dispersant, a stabilizer, a colorant, an opacifier, a sweetener, a taste masking agent, or combination thereof.

Additional objects and advantages of the present invention will become readily apparent to those skilled in this art from the following detailed description, wherein only the preferred embodiment of the invention is shown and described, simply by way of illustration of the best mode contemplated for carrying out the invention. As will be realized, the invention is capable of other and different embodiments and its several details are capable of modifications in various obvious respects, all without departing from the invention. Accordingly, the drawings and description are to be regarded as illustrative in nature, and not as restrictive. The following more detailed description is thus provided.

4. BRIEF DESCRIPTION OF THE FIGURES

5. DETAILED DESCRIPTION OF THE PREFERRED EMBODIMENTS

Citicoline, especially its alkaline salt, is hygroscopic. The hydrated form of citicoline described in the literature is the monohydrate. For example, monohydrate of CDP-choline is disclosed in U.S. Pat. No. 3,687,932 issued to Nakamachi et al. Numerous commercial sources of citicoline exist, including Takeda, Kuoya, Yamasa (all of Japan), Ferrer International (Spain), Pro Bio Sint (Italy) and Sunry (China).

All manufacturers of conventional citicoline have established similar standards/specifications for citicoline, including a limit for water of not more than 5% by weight. Normally the amount of water is between 2 to 4% by weight. The inventor has determined that such conventional forms of citicoline are unstable on exposure to atmospheric humidity. Indeed, it is discovered that when unprotected citicoline is deliberately subjected to high humidity over a prolonged period, it equilibrates in a hyperhydrated state, one in which the citicoline hyperhydrate is found to comprise approximately 12–12.5% (w/w) water. In the hyperhydrated state, the hygroscopic nature of the molecule is suppressed and it exists in a more stable crystalline form. Although the invention is not limited by theory, this percentage of water "theoretically" corresponds to a never-before-described "tetrahydrate" form of citicoline. ("Citicoline sodium tetrahydrate" contains a theoretical amount of water, which is 12.4% by weight.)

Figure 6:
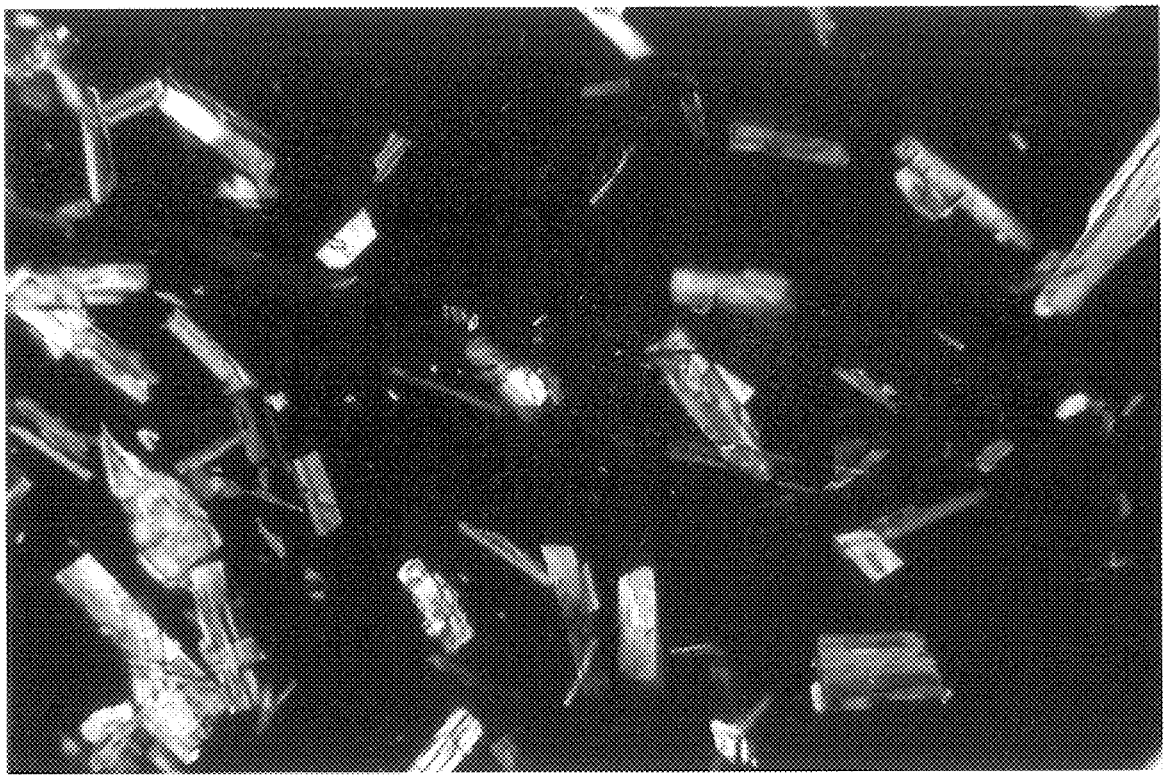
FIG. 6 shows well formed, euhedral, columnar crystals of hyperhydrated citicoline of the present invention.
Figure 7:
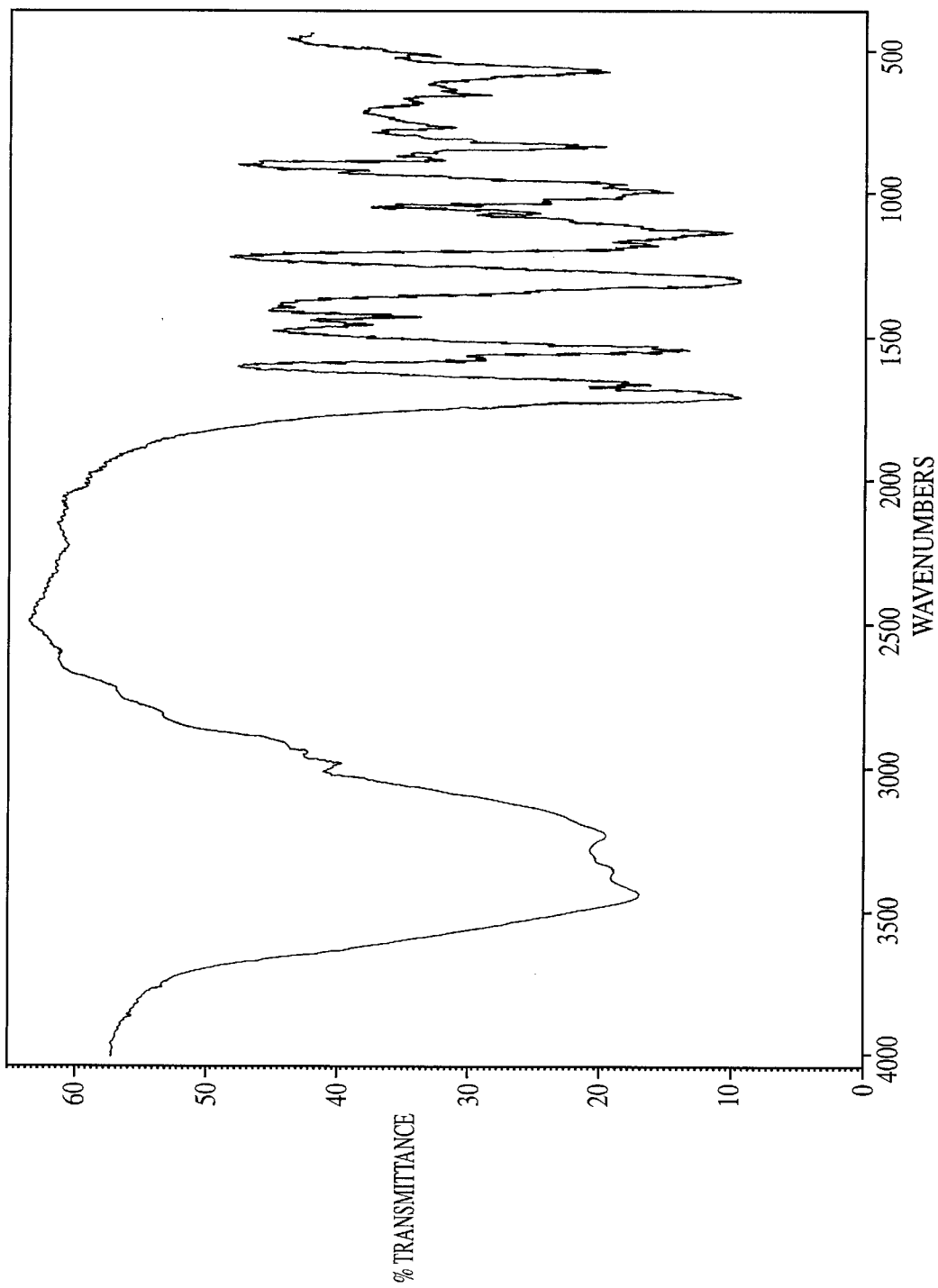
FIG. 7 shows an infrared (KBr pellet) absorption pattern of crystalline hyperhydrated citicoline.

This citicoline tetrahydrate is obtainable in a highly crystalline form (FIG. 6). It is possible that some or all of the water molecules make up waters of crystallization; that is, the water molecules may be partially or entirely taken up within the crystal lattice, tightly associated with the citicoline molecule. It is also possible that all or part of the water is adsorbed onto and resides on the crystal surface. A combination of water within of crystal body and water adsorbed on the crystal surface is, of course, possible.

Several evaluations of citicoline are performed subsequently to confirm the preferred state of hydration of the molecule. Some of the most convincing evidence is obtained from moisture sorption/desorption isotherms. Isotherms are generated for citicoline sodium produced by three commercial manufactures. Similar results are obtained for all. See FIGS. 1–3. Initially, a sample of the low-water-content (<5%) compound is dried to a constant equilibrium weight. The dried material is then slowly exposed to increasingly higher relative humidity (RH), and the change in weight of the sample is recorded. At levels of RH below 40%, citicoline sodium takes up water readily and various states of hydration below the theoretical "tetrahydrate" level are obtainable. However, when the RH approaches 40% RH citicoline sorbs water less readily and appears to be less hygroscopic, reaching an apparent steady state of water content. The water content of the solid sample equilibrates at a level of approximately 10 to about 13% (w/w), preferably about 11 to about 13% (w/w), more preferably, ca. 12–13% (w/w). Between 40–85% RH citicoline sodium remains at this tetrahydrated state. Above 85% RH citicoline sodium sorbs an even higher proportion of water and exhibits deliquescence.

In the reverse direction (moisture desorption; see, triangular isotherms), as RH levels are decreased, citicoline sodium readily loses (or desorbs) water until the sample equilibrates once again at the tetrahydrate state (i.e., approximately 12–13% (w/w) water). The tetrahydrate is observed in the range of about 75–80% RH (at the high end) to about 10% RH (at the low end). Accordingly, the desorption isotherm further demonstrates that a preferred moisture content for citicoline is about 12–13% water by weight.

A second evaluation is performed in which citicoline batch samples from three different commercial suppliers are exposed directly to a high-temperature/high-humidity condition of 40° C. and 75% RH for periods of 24 and 48 hours. At each time interval the percentage of water is determined by Karl Fischer analytical methods. The results for all batches demonstrate that citicoline, in particular, citicoline sodium, sorbs between about 12.2% to about 12.5% by weight water and remains stable at this state of hydration.

Figure 4:
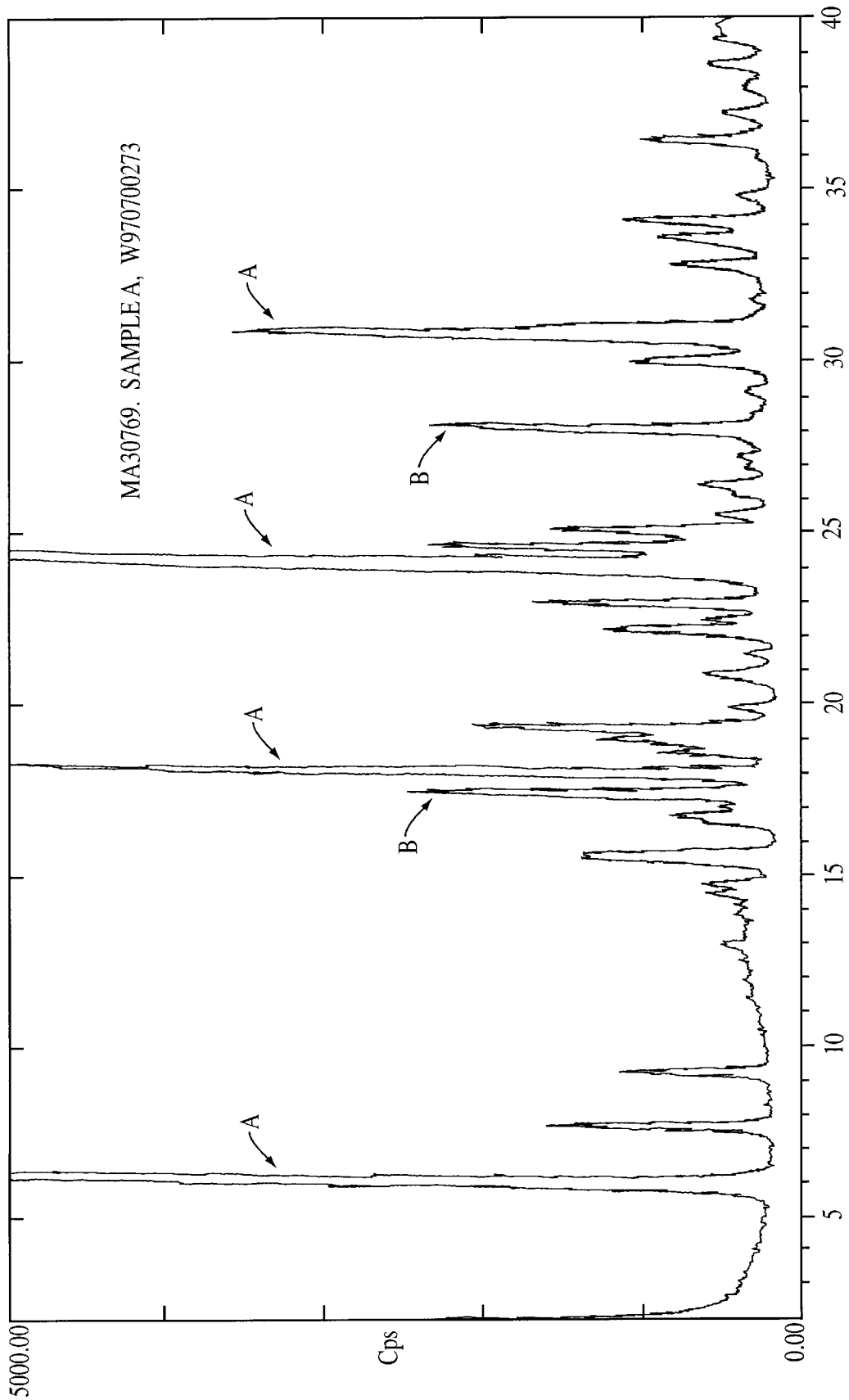
FIG. 4 shows the X-ray powder diffraction pattern of hyperhydrated citicoline sodium of the present invention.

The X-ray diffraction of the citicoline sodium of the present invention (i.e., a sample of hyperhydrated citicoline generated from conventional citicoline sodium from the same supplier) is obtained. The diffraction pattern of the hyperhydrated citicoline of the present invention is illustrated in FIG. 4. The diffraction pattern of hyperhydrated citicoline exhibits significant differences from the X-ray diffraction pattern of the conventional citicoline (see FIG. 2 in U.S. Pat. No. 3,687,932). An analysis of the peak positions and/or intensities of the two diffraction patterns support the notion that the differences are attributable to different states of hydration of the citicoline rather than the existence of different polymorphic forms. Indeed, the "hypohydrate" is less crystalline since in addition to occasional crystals it contains amorphous non-crystal bodies (FIG. 1 in U.S. Pat. No. 3,687,932) while the hyperhydrate exhibits good crystalline characteristics. Representative crystals of citicoline of the instant invention are shown in FIG. 6. The crystal samples are obtained by exposure to high-temperature/high-humidity condition of 40° C. and 75% RH for periods of 24 and 48 hours. Crystals are then dispersed in silicone oil and examined by polarized light microscopy at a magnification of 10×7 using crossed polars and a first order compensator. Well formed euhedral columnar crystals of hyperhydrated citicoline are observed.

Accordingly, the term "hyperhydrate" or "hyperhydrated" is used herein to mean a state of hydration of citicoline, which can be characterized as having a water content in the range of about 10.5–14.5% (w/w), preferably about 11.5–13.5% (w/w), more preferably about 12–13% (w/w) and most preferably about 12.2–12.5% (w/w). As stated elsewhere in the present disclosure, such a hyperhydrated state of citicoline consists essentially of citicoline tetrahydrate.

5.1 Drug Product Formulations

The present invention broadly contemplates a wide variety of drug product formulations that either use the hyperhydrated form of citicoline disclosed herein or which promote the in situ formation of the hyperhydrate within the formulation. Such formulations include solid, powder, crystalline, liquid, emulsion, suspension and like dosage forms prepared using the citicoline hyperhydrate. The various dosage forms can, of course, be administered in a variety of ways, including but not limited to enteral and parenteral modes, transdermal, transmucosal, vaginal, rectal, buccal, intranasal, or like modes. Specifically contemplated by the present invention are oral forms, intravenous, intramuscular, intracavity, intraperitoneal, subcutaneous, intranasal, intraopthalmic, intracraneal, intracardial and like forms. The pharmaceutical forms of the citicoline hyperhydrate can be administered locally, generally, or systemically. The present invention is best exploited, however, by its use in solid dosage forms for the administration to the subject.

For comparative purposes, the manufacture of a tablet formulation containing conventional citicoline is first described. The resulting tablet is relatively unstable upon exposure to atmospheric moisture. Appropriate product packaging must be used in an attempt to retard moisture uptake by the citicoline drug. The manufacturing process requires a relatively low-humidity environment to ensure the low water content qualities of the drug, as suggested by the commercial provider of the drug product. The process involves the mixing of the drug substance and the excipients, including lipids, talc and the like, followed by a compacting step to provide a tablet. The compaction step produces a material that is hard, dense and better described as an amorphous crystal state. The excipients can help retard moisture sorption. The final specification for the moisture content of the tablet is not more than 8% (w/w).

Next, the tablets containing conventional citicoline are exposed to ambient conditions. Eventually, the tablets swell and crack. It is found that the rate and extent of tablet swelling and eventual cracking depends on the RH level of the test condition.

In a preferred embodiment of the present invention, a stable, immediate release, solid, oral dosage form is prepared which contains 522.5 mg of citicoline sodium (an amount equivalent to about 500 mg of the free acid). The preferred dosage form is suitable for clinical use. In contrast to the procedure described above, conventional citicoline starting material may be deliberately hydrated to its equilibrated state. One way to achieve the hyperhydrated state is via a wet granulation process. Over an effective period of time during the wet granulation process, the putative citicoline hyperhydrate is achieved. The following excipients can be used in addition to the citicoline sodium (in units of mg per tablet):

Citicoline sodium 522.5
Magnesium stearate 7.8
Colloidal silicon dioxide 3.9
Croscarmellose sodium 25.0
Microcrystalline cellulose 101.1
Corn starch 50.0
Total Water 89.7

| Excipient | mg/tablet | Est. Residual/Sorbed Water (%) | Est. mg of Water |
|---|---|---|---|
| Magnesium Stearate | 7.8 | 4.0 | 0.3 |
| Colloidal Silicon Dioxide | 3.9 | 2.5 | 0.1 |
| Croscarmellose Sodium | 25.0 | 10.0 | 2.5 |
| Microcrystalline Cellulose | 101.1 | 8.0 | 8.1 |
| Corn Starch | 50.0 | 14.0 | 7.0 |
| TOTAL WATER ASSOCIATED WITH EXCIPIENTS (mg) = | | | 18.0 |

According to the present discovery, one mole of citicoline sodium will sorb about 4 moles of water. Thus, in a tablet containing 522.5 mg of anhydrous citicoline sodium, the drug molecules will sorb 72 mg of water. Therefore, 72 mg+18 mg=90 mg (or 89.7 mg), as listed above for the total amount of purified water contained in a single tablet formulated by the wet-granulation method.

The drying time of the wet granulation process can be controlled to leave a hydrated substance having a moisture level of approximately 11% to 12% water by tablet weight, preferably 11.6% water by tablet weight. On the other hand, increasing the drying time results in a tablet with a moisture content of less than 9% by weight water. Consequently, for such "drier" samples, additional water needs to be added to the formulation to permit the in situ formation of the hyperhydrated citicoline. It appears that the optimum amount of water is approximately 12% by weight water. The tablets of the present invention do not exhibit swelling or cracking over time, have improved shelf life and long term stability.

Once again, after 3 days of exposure to the high moisture environment, the formulation, which does not contain the hyperhydrated state of citicoline, becomes very soft (the tablet hardness decreases to 2 Kp, meaning that one can easily crush this tablet) and appears swollen and cracked. In contrast, the formulation produced with the wet granulation method of the present invention does not show any signs of swelling and/or cracking, although in some cases the hardness of the tablet decreases to 8.1 Kp. Preferably, the formulation of the present invention can maintain hardness in the range of about 8 to about 15 Kp, more preferably in the range of about 9 to about 14 Kp, most preferably in the range of about 10 to about 13 Kp. Most importantly, the initial hardness should be maintained substantially over time. Optimization can provide the desired hardness levels depending on one's requirements. Once again, the tablet of the invention is stable. It does not sorb significant amounts of moisture over extended periods.

5.2 Capsule Development

A soft-gelatin capsule of superior integrity and storage stability is also made possible by the present invention. Experiments conducted in the development phase demonstrate that the most stable dosage form is obtained only if the drug is permitted to sorb an amount of water equivalent to that present in the theoretical "tetrahydrate." Indeed, if the drug is formulated as a suspension in an oil matrix, which presumably does not provide moisture to the drug, on aging, the drug will seek to obtain moisture from the gelatin shell. This process produces a capsule that is hard and brittle and which cracks at the seams.

The normal level of water, which the gelatin shell contains for a typical soft-gelatin product, is approximately 6 to 8% water by weight of the gelatin shell. Various amounts of water can be introduced into the fill formulation, with a preferred fill formula containing about 6.5% (w/w) water. Below is the composition of a preferred capsule fill (in units of mg per capsule), in which the hyperhydrated citicoline sodium exists as a suspension:

Citicoline sodium 522.5

Soy bean oil 443.0

Gelucire 44/14 20.0

Lecithin 8.0

Total water 69.5

Moisture levels are determined during stability evaluations of the product and consistent values, equivalent to approximately 12% (w/w) water (based on the weight of citicoline sodium), are recorded. Gelucire 44/14 of this Example is a polyglycolysed glyceride. Other Gelucire equivalents consisting of C8–C18 glycerides and polyethylene glycol esters are used with the same success, e.g., LABRASOL, Gelucire 35/10, Gelucire 37/02, or WL 2514CS.

5.3 Preferred Manufacturing Conditions

A wet granulation method for preparing tablets or capsules containing citicoline is described further below. As a consequence of the preferred manufacturing process of the invention, the state of hydration of the drug is deliberately changed to one that is much more stable. In particular, the resulting product is less hygroscopic, more stable to environmental conditions and does not have extensive packaging requirements to preserve its chemical and physical properties.

Active ingredient(s), diluent(s), disintegrant(s) and other excipients are mixed or blended well using a suitable mixer or blender. Examples of suitable mixers and blenders include, but are not limited to, planetary mixers, high-shear mixers, or twin-shell blenders. Further, examples of diluents and the like include, but are not limited to, corn starch, croscarmellose sodium, microcrystalline cellulose and the like. Afterwards, the resulting powder mass is "wetted" with a suitable amount of water, typically in excess of that required to hydrate the citicoline sodium to a 9–15% (w/w) level, and to produce a suitable mass consistency. The wet granulation may be screened with a comminuting mill or high-speed mixer. Then, the granulation is dried by, for example, tray drying or a fluid-bed drying. In drying the granulation, it is preferable to maintain a residual amount of moisture in the granulation to permit the citicoline sodium to maintain the 9–15% (w/w) water level. Typically, the wet granulation is dried to a 8–12% (w/w) water level or content, but this may vary depending on the excipients used to formulate the tablet.

Figure 5:
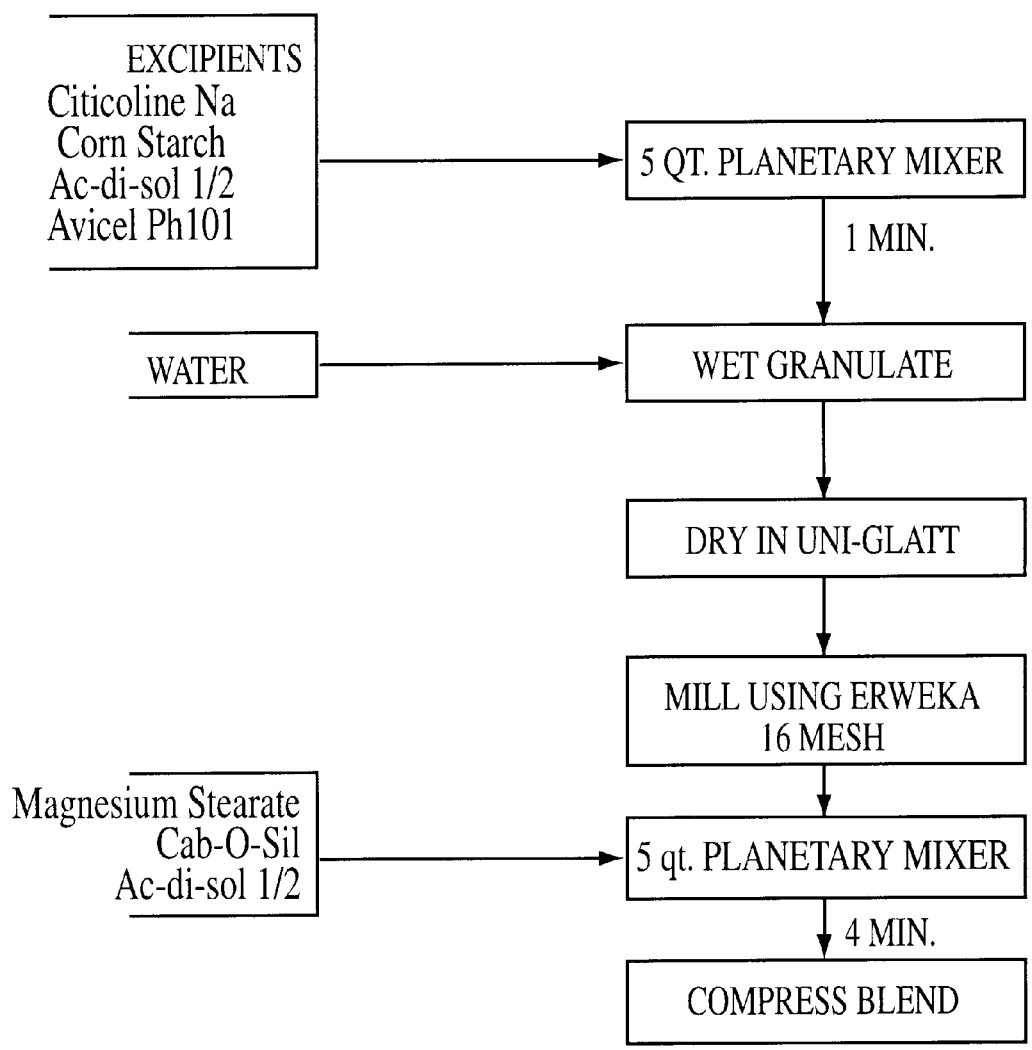
FIG. 5 shows a flow chart of a "wet" granulation process of the invention.

After drying, the granulation is reduced in particle size by passing it through a screen or using a comminuting mill. Additional excipients/lubricants may be added as, for example, croscarmellose sodium. The resulting mixture is then blended using a suitable mixer, such as a planetary mixer or "v"-blender. Suitable lubricants are added at this step, which may include but are not limited to magnesium stearate, and/or silicon dioxide. The resulting granulation is then compressed into tablets or filled into capsules. FIG. 5 provides a flow chart of a "wet" granulation method of the present invention.

Also provided herein is an alternate method of preparation. The citicoline drug is allowed to sorb water to a level of about 10–15% (w/w). The sorption of water by the active ingredient is accomplished by exposure to atmospheric or environmentally controlled moisture conditions, preferably at a moisture level greater than about 30% RH. The time required to achieve a hydration state equivalent to about 10 to about 15% (w/w) water may vary. In particular, the applicable time period may depend on the relative humidity and exposed surface area of the drug. One can determine by a routine experimentation when the drug sample reaches the desired levels of hydration.

Once the drug is hydrated sufficiently, diluent(s), disintegrant(s), filler(s) and/or lubricant(s) are mixed or blended well using a suitable mixer or blender, such as, but not limited to, a "v"-blender, planetary mixer, or twin-shell blender. Examples of general excipients include, but are not limited to, magnesium stearate, silicon dioxide, microcrystalline cellulose, croscarmellose sodium, and the like. Additional lubricants, disintegrants, and/or diluents, such as talc, magnesium stearate, silicon dioxide, microcrystalline cellulose, croscarmellose sodium and the like are added and blended. The resulting material is compressed into tablets or filled into capsules. The resulting product is stable to environmental conditions and does not have extensive packaging requirements.

The tablets of the present invention may comprise one or more inert conventional carriers and/or diluents. Examples, as already mentioned above, include, but are not limited to starch, corn starch, lactose, glucose, sucrose, maltose, microcrystalline cellulose, dicalcium phosphate, stearic acid, magnesium stearate, poly(vinylpyrrolidone), citric acid, tartaric acid, gum tragacanth or gelatin ethoxylated isostearyl alcohols, polyoxyethylene sorbitol and sorbitan esters, aluminum metahydroxide, bentonite, agar-agar, tragacanth, croscarmellose sodium, colloidal silicon dioxide, and mixtures thereof.

The inert conventional carriers and/or diluents in the tablets of the present invention may be present in a variety of ranges. Further additives conventionally employed in the preparation of pharmaceutical tablets may also be incorporated, provided they are not inconsistent with the objectives of the present invention.

The capsules of the present invention may likewise comprise one or more inert conventional carriers, vehicles, and/or diluents. Preferred carriers, vehicles, and/or diluents such as vegetable oils, such as peanut and soybean oil, lecithin, polyoxyethylene stearate, water, albumin, and Gelucire (glycerides and partial polyglycerides of fatty acids), and mixtures thereof. Examples of oils include, but are not limited to, a lipid selected from the group consisting of soybean oil, cotton seed oil, linseed oil, sesame oil, corn oil, peanut oil and safflower oil, triolein, trilinolein, tripalmitin, tristearin, trimyristin, triarachidonin, and a cholesterol ester. Other lipid groups such as a phospholipid, a glycolipid, a stearyl glucoside, stearyl amine, and dicetyl phosphate can be used. In general any polyol esters and glycerides of oil fatty acids are acceptable.

Some preferred hydrophobic materials may include glyceryl monostearates; glyceryl monopalmitates; mixtures of glyceryl monostearate and glyceryl monopalmitate; glyceryl monolinoleate; glyceryl monooleate; mixtures of glyceryl monopalmitate, glyceryl monostearate, glyceryl monooleate and glyceryl monolinoleate; glyceryl monolinolenate; glyceryl monogadoleate; mixtures of glyceryl monopalmitate, glyceryl monostearate, glyceryl monooleate; glyceryl monolinoleate, glyceryl monolinolenate and glyceryl monogadoleate; acetylate monoglycerides; mixtures of propylene glycol monoesters, distilled monoglycerides, sodium stearoyl lactylate and silicon dioxide; mixtures of propylene monoesters, distilled monoglycerides, sodium stearoyl lactylate and silicon dioxide; d-alpha tocopherol polyethylene glycol 1000 succinate; mixtures of mono- and di-glyceride esters; calcium stearoyl lactylate; ethoxylated mono- and di-glycerides; lactated mono- and diglycerides; lactylate carboxylic acid esters of glycerol and propylene glycol; lactylic esters of long chain carboxylic acids; polyglycerol esters of long chain carboxylic acids; propylene glycol mono- and di-esters of long chain carboxylic acids; sodium steroyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; stearyl octanoate; C10–C30 cholesterol/lavosterol esters; and sucrose long chain carboxylic acid esters or mixture thereof.

The inert conventional carriers and/or diluents in the capsules of the present invention may be present in conventional ranges. It may further contain at least one additive group consisting of an excipient, a binder, a disintegrator, a lubricant, a glidant, a wetting agent, an emulsifier, a preservative, an antioxidant, an isotonizing agent, a buffer, a coating agent, a granulating agent, a filler, a bulking agent, a plasticizer, a corrigent, a solution adjuvant, a base, a dispersant, a diluent, a thickener, a stabilizer, a colorant, an opacifier, a sweetener, and a taste masking agent.

One skilled in the art would know how to select specific chemical entities that fall into the above-named categories of additive groups. For example, a dispersant can be selected from the group consisting of croscarmellose sodium, sodium starch glycolate, pregelatinized cornstarch and crospovidone. A binder can be selected from the group consisting of hydroxypropylcellulose, polyvinyl pyrrolidone, polyethylene glycol, and methyl cellulose, while disintegrator is selected from the group consisting of carboxy methyl cellulose, calcium salt of carboxy methyl cellulose, and sodium crosscarmelose. A granulating agent and/or sweetener can be selected from the group consisting of mannitol, sorbitol, dextrose, sucrose, and lactose. A plasticizer and/or coating can be dibutylsebacate and/or various citric acid esters. A sustained-release substance can be selected from the group consisting of hydroxypropylmethyl cellulose, microcrystalline cellulose, hydroxyethyl cellulose, sodium carboxymethyl cellulose, low substituted hydroxypropyl cellulose, a gum arabic, gelatin and shellac. A water-dispersible excipient can be selected from the group consisting of crystalline cellulose, cornstarch, silicic acid, magnesium silicate, and aluminum silicate. These additives are preferably pharmaceutically inert or can have synergistic or additive effects complementing the therapeutic activity of citicoline. Other chemical entities can be selected according to the requirements of the art.

The form of a formulation may consist of a tablet, a capsule, a granule, a powder, a fine granule, a beadlet, a pill, a troche, a buccal, a suppository, an ampoule, a dragee, a cachet, or a lozenge, a salve, or a sachet.

A pharmaceutical citicoline composition may be also in form of microfine powder for insufflation or inhalation, which may additionally contain an adequate amount of bronchodilator. Stabilized citicoline can be further used for formulation of an ointment, an injection, an emulsion, a suspension, or a syrup. Further additives, shapes and sizes of formulation conventionally employed in the preparation of pharmaceutical capsules may also be incorporated, provided they are not inconsistent with the objectives of the present invention.

6. EXAMPLES

The Examples that follow are intended to provide a further illustration of the invention only and should not be construed as limiting the invention in any way. In particular, while the sodium salt of citicoline is described in the following examples, the free acid, ester, or other salts of citicoline can be used to prepare a hyperhydrated form of citicoline. Such other hyperhydrated citicoline compounds can be utilized in the pharmaceutical dosage forms, including tablet, caplet, soft gelatin capsule, or the like. Preferred forms of citicoline are the alkaline salts of citicoline including, but not limited to, the sodium or potassium salts thereof.

6.1 Preparation of Citicoline Hyperhydrate

Citicoline hyperhydrate or citicoline tetrahydrate is prepared as follows:

Conventional citicoline is dried to an anhydrous state. The theoretical amount of water or slight excess is added to provide a combination, which is mixed in a mixer that permits control over the humidity. Alternatively, the mixer can be equipped with a spray jet to apply the adequate amount of water.

In another procedure, the conventional citicoline is allowed to equilibrate to its hyperhydrated state under the appropriate humidity or moisture conditions. The citicoline hyperhydrate is then used to provide the stable formulation of the present invention. As mentioned elsewhere, in this disclosure the conventional citicoline can be formulated to provide a stable formulation of the present invention by providing an adequate amount of water in the formulation to permit the in situ formation of the citicoline hyperhydrate. See, also, the description found in EP 329627 A2 for the different salts of citicoline, which are readily available.

6.2 Generation of Sorption/Desorption Isotherm

Figure 1:
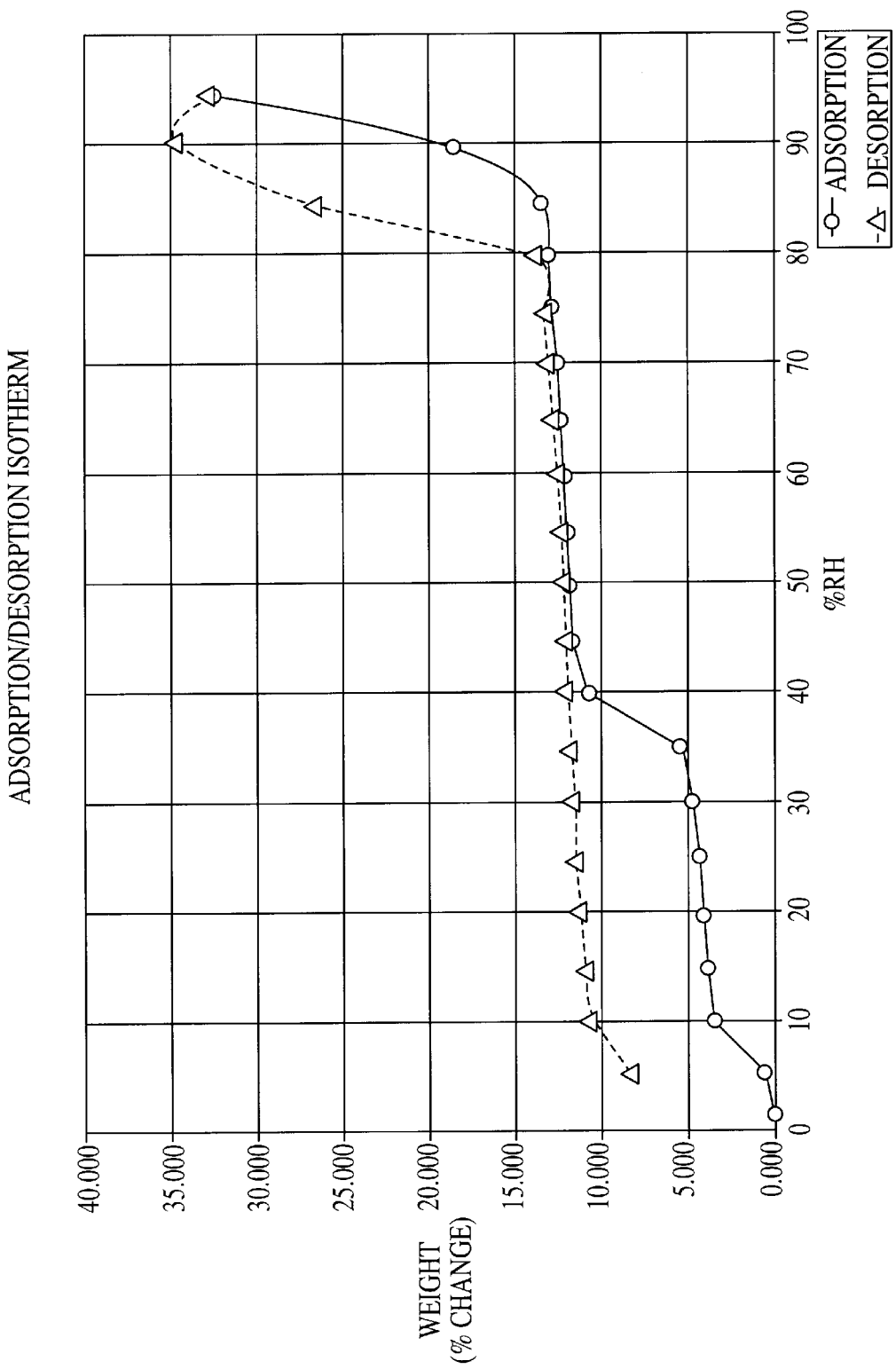
FIG. 1 shows the sorption/desorption isotherm of citicoline sodium obtained from commercial manufacturer No. 1.

A moisture sorption/desorption isotherm is generated for citicoline sodium obtained from a commercial manufacturer from Japan. A sample of citicoline sodium is dried to a constant equilibrium weight. Then, the sample is slowly exposed to increasingly higher relative humidity (RH) and the weight change of the sample is recorded. The results are shown in FIG. 1. Below 40% RH, the sample apparently exists in various hydration states. As 40% RH is approached, the sample readily sorbs water and equilibrates at a level of about 12–13% (w/w) water. Between 40 to 85% RH, the sample remains in this state. Above 85% RH, the sample sorbs a high percentage of water and exhibits deliquescence. As RH levels are decreased, the sample loses water until it again reaches a state of equilibration at a level of about 12–13% (w/w) water. This level of water content remains relatively stable down to a 10% RH level.

6.3 Additional Moisture Sorption/Desolption Study

Figure 2:
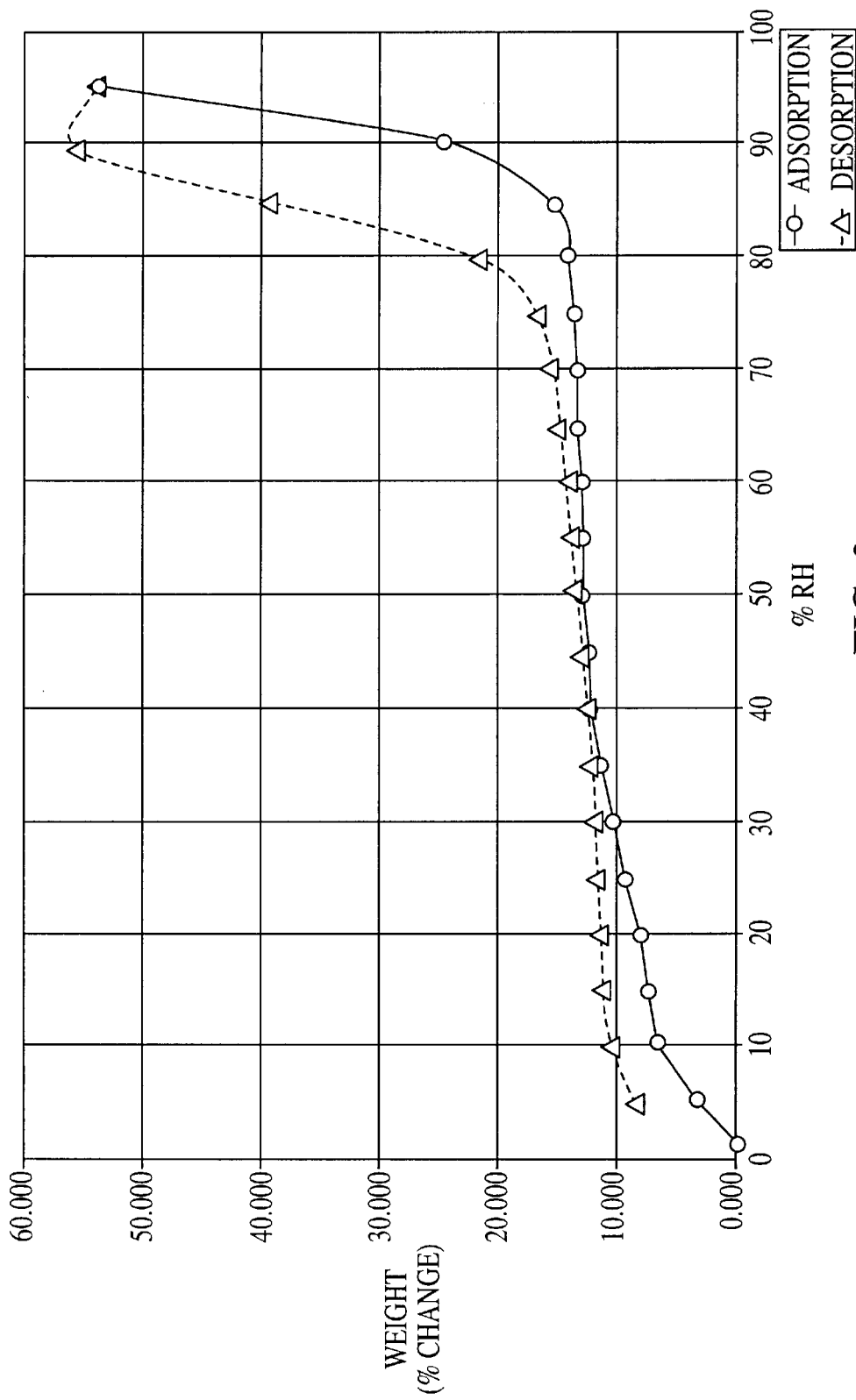
FIG. 2 shows the sorption/desorption isotherm of citicoline sodium obtained from commercial manufacturer No. 2.

A moisture sorption/desorption isotherm is generated for citicoline sodium obtained from a commercial manufacturer from Europe, in accordance with the procedure described in Example 6.2, above. The results are shown in FIG. 2. The isotherm shows that a preferred moisture content level for the material is about 12–13% water.

6.4 Yet Another Moisture Sorntion/Desorption Study

Figure 3:
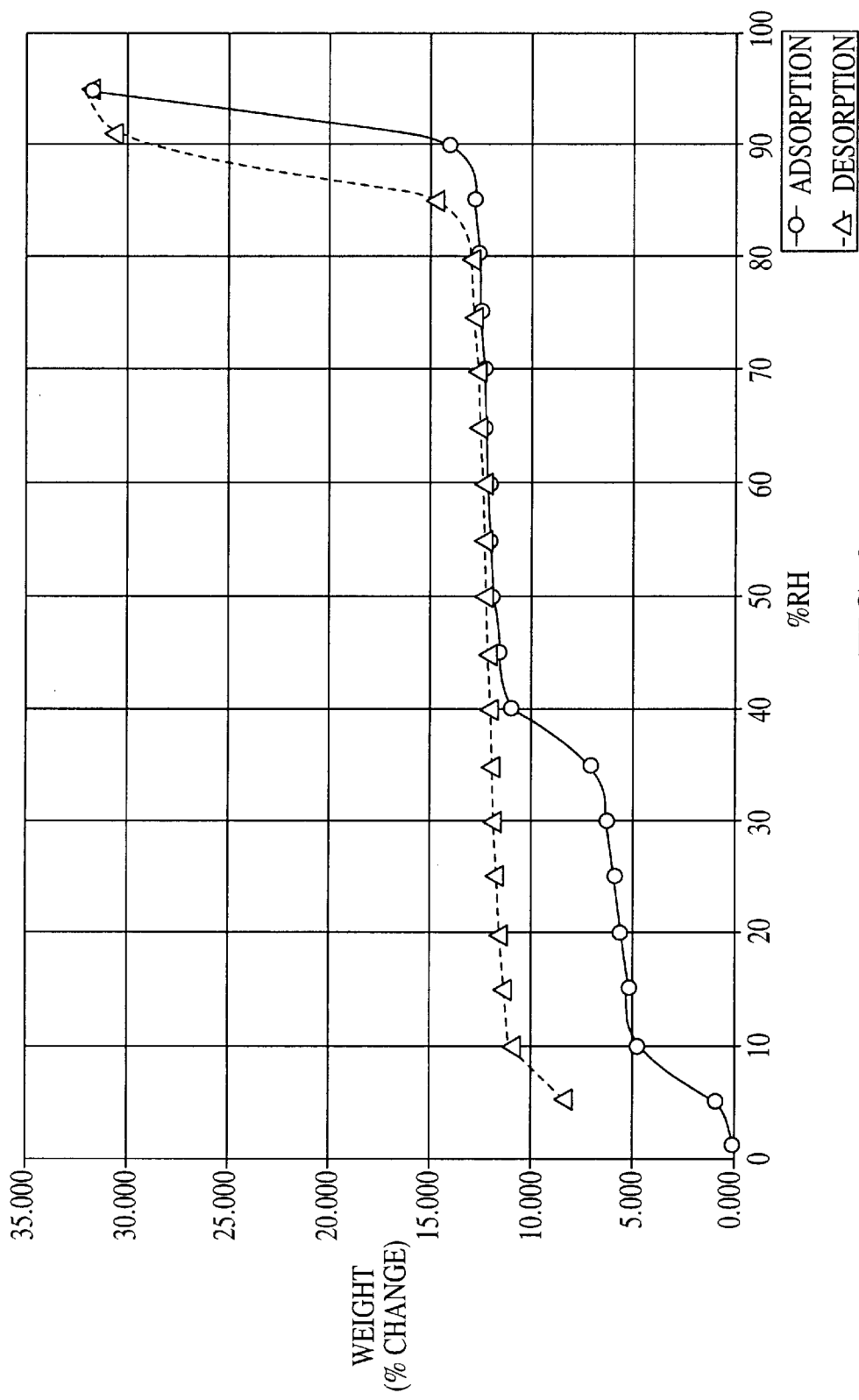
FIG. 3 shows the sorption/desorption isotherm of citicoline sodium obtained from commercial manufacturer No. 3.

A moisture sorption/desorption isotherm is generated for citicoline sodium obtained from a commercial manufacturer from the Far East, in accordance with the procedure described in Example 6.2, above. The results are shown in FIG. 3. The isotherm shows that a preferred moisture content level for the material is about 12–13% water.

6.5 Studies Under High Temperature/Humidity Conditions

Samples of a citicoline sodium, which are obtained from each of three manufacturers mentioned above, are directly exposed to a high temperature/humidity condition of 40° C./75% RH for periods of 24 and 48 hours. At each time interval, the percentage of water is determined using Karl Fischer analytical techniques. The results are shown in the Table 1. The results for all batches demonstrate that under these conditions conventional samples of citicoline sodium sorbs between 12.2–12.5% water and remain stable at this state.

TABLE 1

Percent Moisture Testing for Citicoline Bulk Drug Substance

| Lot | Initial Moisture % (w/w) | Average % Moisture (w/w) | |
|---|---|---|---|
| | | 24 Hours | 48 Hours |
| Manuf. No. 1 | 2.910 | 12.53 | 12.50 |
| Manuf. No. 2 | 2.944 | 12.43 | 12.53 |
| Manuf. No. 3 | 3.311 | 12.32 | 12.20 |

High Temperature/Humidity Condition: 40° C./75% RH 6.6 X-Ray Powder Diffraction Studies X-ray powder diffraction patterns are generated on a batch of citicoline sodium sample of the present invention, having a water content of about 12.2–12.5%. The X-ray powder diffraction is carried out using a Siemens D5000 Diffractometer with a copper radiation source. The results for the hyperhydrated sample are illustrated in FIG. 4. The "conventional" citicoline sodium exhibits an X-ray powder diffraction pattern that is consistent with a sample that is less crystalline and more amorphous in nature. In contrast, the X-ray powder diffraction pattern of the citicoline sodium hyperhydrate of the invention is consistent with a sample that is much more crystalline. Further, the differences in the peak positions appear to be due more to the existence of different hydration states rather than different polymorphic forms.

Patterns of X-ray powder diffraction for the tetrahydrate of citicoline sodium are shown in FIG. 4. At least some of the characteristic diffractometric peaks are indicated with the arrows (A and B).

6.7 Tablet Formulation Under Wet Granulation Conditions

A stable, imrnediate-release, solid oral dosage tablet, which contains 552.6 mg of citicoline sodium (equivalent to 500 mg of the free acid), is prepared using a wet granulation process. A flow chart, summrarizing this process, is shown in FIG. 5. A preferred tablet is comprised of the following components (in units of milligrams):

Citicoline sodium 522.5
Magnesium stearate 7.8
Colloidal silicon dioxide 3.9
Croscarmellose sodium 25.0
Microcrystalline sodium 120.8
Corn starch 100.0
Total Water 98.6

Other tablet formulations are readily contemplated based on the insight provided by the present invention, which includes assuring the presence of an adequate amount of water proportional to 12% by weight water based on the amount of citicoline present in the desired formulation.

6.8 Stability Studies

Tablets from Example 6.7 are evaluated for stability. The tablets are directly exposed to a high moisture environment (40° C./75% RH) for two weeks. The tablets produced with the wet granulation process of the invention do not show any signs of swelling and/or cracking.

6.9 Soft Gelatin Capsule Formulation

A soft gelatin capsule is prepared. The final formula contains about 12% water, based on the weight of citicoline sodium. Below is the composition of the capsule fill (in units of milligrams per capsule):

Citicoline sodium 522.5
Soy bean oil 459.5
Gelucire 44/14 20.0
Lecithin 8.0
Purified water 70.0

Moisture levels are determined during stability evaluations of the capsule and consistent values, equivalent to approximately 12% (based on the weight of citicoline sodium), are recorded. Preferred polyglycolysed glyceride is Gelucire 44/14. However, other Gelucire equivalents consisting of C8–C18 glycerides and polyethylene glycol esters are used with the same success, e.g., LABRASOL, Gelucire 35/10, Gelucire 37/02, or WL 2514CS.

6.10 Additional Tablet Formulation

A tablet that contains 539 mg of citicoline potassium (equivalent to 500 mg of the free acid) is prepared using roller compaction or wet granulation conditions. The citicoline drug is formulated with lactose, dicalcium phosphate and other excipients. The tablet comprises the following components (in units of milligrams per tablet):

Citicoline potassium 539
Magnesium stearate 7.8
Colloidal silicon dioxide 3.9
Croscarmellose sodium 25.0
Microcrystalline sodium 101.1
Corn starch 50
Purified water 90.0

In the present description, numerous specific details are set forth, such as specific structures, chemicals, processes, etc., to provide an adequate understanding of the present invention. However, as one having ordinary skill in the art would recognize, the present invention can be practiced without resorting to the examples or preferred embodiments specifically set forth. Optimization of the particular embodiments described is also within the reach of one of ordinary skill in the art. It is further understood that the invention is capable of use in various other combinations and environments and includes changes and/or modifications apparent to those of ordinary skill. The invention is not to be limited to the examples provided. It is limited solely by the claims that follow.

What is claimed is:

1. A solid hyperhydrated form of citicoline having a water content of not less than about 10% by weight.

2. The citicoline of claim 1 having a water content of not less than about 10.5% by weight.

3. The citicoline of claim 1 having a water content of not less than about 11% by weight.

4. The citicoline of claim 1 having a water content of not less than about 12% by weight.

5. The citicoline of claim 1 having a water content that ranges from about 10% to about 15% by weight.

6. The citicoline of claim 5 having a water content that ranges from about 10.5% to about 14% by weight.

7. The citicoline of claim 5 having a water content that ranges from about 11% to about 13% by weight.

8. The citicoline of claim 5 having a water content that ranges from about 12% to about 13% by weight.

9. The citicoline of claim 1 which comprises an alkaline salt of citicoline.

10. The citicoline of claim 9 which comprises citicoline sodium.

11. The citicoline of claim 9 which comprises citicoline potassium.

12. The citicoline of claim 10 having a water content that ranges from about 12% to about 13% by weight.

13. The citicoline of claim 12 having a water content of about 12.5% by weight.

14. The citicoline of claim 1 in which said citicoline is an acid addition salt comprising a salt-forming moiety which is a hydrochloric acid, a hydrobromic acid, a sulfonic acid, a sulfuric acid, a acetic acid, a triflouroacetic acid, a citric acid, a lactic acid, a malonic acid, a tartaric acid, an acrylic acid, a methacrylic acid, a malic acid, a maleic acid, a fumaric acid, a benzoic acid, a salicylic acid, a cinnamic acid, a methanesulfonic acid, a benzenesulfonic acid, a toluenesulfonic acid, or nicotinic acid.

15. The citicoline of claim 14 having a water content that ranges from about 12% to about 13% by weight.

16. The citicoline of claim 15 having a water content of about 12.5% by weight.

17. The citicoline of claim 1 in which said citicoline is covalently bound to a polymeric matrix containing carboxy groups and said polymeric matrix is a polyacrylic acid, polymethacrylic acid, polymaleic acid, polyaminoacid, or copolymers of polymerizable acids with acrylic acid or acrylamide.

18. The citicoline of claim 17 having a water content that ranges from about 12% to about 13% by weight.

19. The citicoline of claim 18 having a water content of about 12.5% by weight.

20. A hyperhydrated form of citicoline which exhibits an X-ray powder diffraction pattern having characteristic diffractometric peaks at least those falling substantially at peak positions 6, 18, 24.3 and 31.2.

21. The hyperhydrated form of citicoline of claim 20 which exhibits additional peaks falling substantially at peak positions 17.5 and 28.3.

22. The hyperhydrated citicoline of claim 20 which comprises a citicoline sodium hyperhydrate or citicoline potassium hyperhydrate.

23. The citicoline of claim 1 which exhibits a change in weight of less than about 2% upon exposure to moisture conditions having a relative humidity (RH) ranging from about 10% to about 80%.

24. A formulation comprising citicoline having a total water content sufficient to provide an amount of water which is not less than about 10.5% by weight relative to the amount of citicoline present in the formulation.

25. The formulation of claim 24 having a total water content sufficient to provide an amount of water which is not less than about 11.5% by weight relative to the amount of citicoline present in the formulation.

26. The formulation of claim 24 having a total water content sufficient to provide an amount of water which is not less than about 12.5% by weight relative to the amount of citicoline present in the formulation.

27. The formulation of claim 24 which is a tablet, a capsule, a granule, a powder, a beadlet, a pill, a troche, a buccal, a suppository, an ampoule, a dragee, a sachet, a cachet, a salve, or a lozenge.

28. The formulation of claim 24 which further contains an additive group which is an excipient, a binder, a disintegrator, a lubricant, a glidant, a wetting agent, an emulsifier, a diluent, a thickener, a preservative, an antioxidant, an isotonizing agent, a buffer, a coating agent, a granulating agent, a filler, a bulking agent, a plasticizer, a corrigent, a solution adjuvant, a base, a dispersant, a stabilizer, a colorant, an opacifier, a sweetener, a taste masking agent, or combination thereof.

* * * * *